(12) United States Patent
Garthaffner

(10) Patent No.: US 10,858,137 B2
(45) Date of Patent: Dec. 8, 2020

(54) SYSTEM AND METHOD FOR APPLYING A LABEL FOR THE AUTOMATED PRODUCTION OF E-VAPOR DEVICES

(71) Applicant: Altria Client Services LLC, Richmond, VA (US)

(72) Inventor: Martin Garthaffner, Chesterfield, VA (US)

(73) Assignee: Altria Client Services LLC, Richmond, VA (US)

( * ) Notice: Subject to any disclaimer, the term of this patent is extended or adjusted under 35 U.S.C. 154(b) by 766 days.

(21) Appl. No.: 14/972,791

(22) Filed: Dec. 17, 2015

(65) Prior Publication Data
US 2016/0176564 A1 Jun. 23, 2016

Related U.S. Application Data

(60) Provisional application No. 62/094,743, filed on Dec. 19, 2014.

(51) Int. Cl.
*B65C 3/04* (2006.01)
*B65C 9/18* (2006.01)
(Continued)

(52) U.S. Cl.
CPC .............. *B65C 3/04* (2013.01); *A24F 47/002* (2013.01); *B65C 7/00* (2013.01); *B65C 9/1807* (2013.01);
(Continued)

(58) Field of Classification Search
CPC .. B65C 3/04; B65C 3/065; B65C 3/12; B65C 9/36; B65C 3/02; B65C 9/02; B65C 9/26; B65B 11/30; A24C 5/327; A61M 15/06
See application file for complete search history.

(56) References Cited

U.S. PATENT DOCUMENTS 2,809,640 A 10/1957 Oldenkamp
3,506,017 A * 4/1970 Schubert ................ A24C 5/471
131/94

(Continued)

FOREIGN PATENT DOCUMENTS

CN 1046664 A 11/1990
CN 1094372 A 11/1994
(Continued)

OTHER PUBLICATIONS

Non-Final Office Action dated Aug. 2, 2017 in copending U.S. Appl. No. 14/883,980.
(Continued)

*Primary Examiner* — Carson Gross
(74) *Attorney, Agent, or Firm* — Harness, Dickey & Pierce, P.L.C.

(57) ABSTRACT

A system for use in manufacturing vapor-generating articles may include a rotatable drum that is configured to hold a plurality of the vapor-generating articles. The system may also include a tagging drum that is configured to tag a respective label to a housing of each of the vapor-generating articles. The system may also include a pressing roller that is configured to press a leading edge of the label against the housing after the tagging. The system may further include a rolling drum that is configured to roll the label around the housing after the pressing.

20 Claims, 9 Drawing Sheets

(51) Int. Cl.
  *A24F 47/00* (2020.01)
  *B65C 7/00* (2006.01)
  *B65C 9/30* (2006.01)
  *A61M 15/06* (2006.01)
  *B65C 9/02* (2006.01)
  *A24C 5/32* (2006.01)

(52) U.S. Cl.
  CPC .............. *B65C 9/30* (2013.01); *A24C 5/327* (2013.01); *A61M 15/06* (2013.01); *B65C 9/02* (2013.01)

(56) References Cited

U.S. PATENT DOCUMENTS

| | | | |
|---|---|---|---|
| 3,811,567 A | 5/1974 | Tomita et al. | |
| 3,837,378 A | 9/1974 | Kanki et al. | |
| 3,961,633 A * | 6/1976 | Schubert | A24D 3/0287 131/94 |
| 3,986,320 A | 10/1976 | Bausch et al. | |
| 4,545,832 A * | 10/1985 | Hoffmann | B29C 63/40 156/294 |
| 4,980,969 A | 1/1991 | Marchesini et al. | |
| 5,024,046 A * | 6/1991 | Spatafora | B65B 11/30 53/216 |
| 5,024,242 A * | 6/1991 | Garthaffner | A24C 5/00 131/280 |
| 5,116,298 A | 5/1992 | Bondanelli et al. | |
| 5,390,469 A * | 2/1995 | Shimizu | B65B 3/003 53/280 |
| 5,464,495 A | 11/1995 | Eder | |
| 5,577,518 A * | 11/1996 | Draghetti | A24C 5/471 131/32 |
| 5,702,559 A * | 12/1997 | Bright | B41J 3/32 156/212 |
| 5,772,001 A * | 6/1998 | Otruba | B65G 47/846 198/459.2 |
| 6,450,230 B1 * | 9/2002 | Otruba | B65C 9/1807 156/542 |
| 6,708,694 B2 * | 3/2004 | Dombek | A24C 5/471 131/27.1 |
| 7,296,578 B2 * | 11/2007 | Read, Jr. | A24C 5/471 131/106 |
| 8,828,170 B2 * | 9/2014 | Stamatiou | B32B 27/10 156/243 |
| 9,828,130 B2 * | 11/2017 | Florian | B65C 3/16 |
| 9,963,260 B2 * | 5/2018 | Cadieux | A24F 47/008 |
| 9,968,131 B2 * | 5/2018 | Swepston | A24F 47/002 |
| 2002/0005207 A1 | 1/2002 | Wrenn et al. | |
| 2004/0020500 A1 | 2/2004 | Wrenn et al. | |
| 2005/0217207 A1 | 10/2005 | Konishi et al. | |
| 2008/0017203 A1 | 1/2008 | Fagg et al. | |
| 2012/0167906 A1 | 7/2012 | Gysland | |
| 2013/0199550 A1 | 8/2013 | Ono | |
| 2014/0041655 A1 | 2/2014 | Barron et al. | |
| 2015/0272204 A1 | 10/2015 | Kraisuwannasarn | |
| 2017/0006921 A1 | 1/2017 | Lemay et al. | |

FOREIGN PATENT DOCUMENTS

| | | |
|---|---|---|
| CN | 1203699 A | 12/1998 |
| CN | 1268470 A | 10/2000 |
| CN | 101310632 A | 11/2008 |
| CN | 201758770 U | 3/2011 |
| CN | 102177071 A | 9/2011 |
| CN | 202603608 U | 12/2012 |
| CN | 203015835 U | 6/2013 |
| CN | 103369979 A | 10/2013 |
| CN | 103491812 A | 1/2014 |
| CN | 103584287 A | 2/2014 |
| DE | 1532561 A1 | 4/1970 |
| DE | 3117999 A1 | 11/1982 |
| DE | 202006006452 U1 | 7/2006 |
| EP | 0330495 A2 | 8/1989 |
| EP | 0395280 A2 | 10/1990 |
| EP | 0544089 A2 | 6/1993 |
| EP | 0579026 A1 | 1/1994 |
| JP | 2005247325 A | 9/2005 |
| WO | WO-2013002657 A1 | 1/2013 |
| WO | WO-2013076750 A1 | 5/2013 |
| WO | WO-2015/123558 A2 | 8/2015 |
| WO | WO-2015160809 A1 | 10/2015 |

OTHER PUBLICATIONS

Third Party Observation issued in European Application No. 15791025.8 dated Aug. 18, 2017.
Ampoule, from Wikipedia, the free encyclopedia, retrieved from https://en.wikipedia.org/w/index/php?title=Ampoule&oldid=784220607, page last edited Jun. 7, 2017.
Vial, from Wikipedia, the free encyclopedia, retrieved from https://en.wikipedia.org/w/index/php?title=Vial&oldid=771730942, page last edited Mar. 23, 2017.
International Preliminary Report on Patentability issued in International Application No. PCT/US2015/025754, dated Oct. 27, 2016.
International Preliminary Report on Patentability issued in International Application No. PCT/IB2015/001477, dated Oct. 27, 2016.
Office Action for corresponding Eurasian Application No. 201692055 dated Feb. 20, 2019.
Chinese Office Action dated Aug. 30, 2017 for corresponding Chinese Patent Application No. 201580031588.
Office Action for copending U.S. Appl. No. 14/686,519 dated Jun. 7, 2017.
Office Action for corresponding Eurasian Application No. 201692054 dated Jul. 26, 2018 and English translation thereof.
International Preliminary Report on Patentability issued in International Application No. PCT/US2015/066290, dated Jun. 20, 2017.
European Office Action dated Sep. 28, 2018 in corresponding Application No. 15791025.8.
Office Action for corresponding U.S. Appl. No. 14/686,431 dated Nov. 1, 2017.
Office Action for corresponding Chinese Application No. 201580069381.1 dated Nov. 2, 2018.
International Preliminary Report and Written Opinion of the International Searching Authority dated Apr. 27, 2017, issued in corresponding International Application No. PCT/US2015/055667.
Search Report for corresponding European App. No. 15791025.8 dated Nov. 2, 2017.
Third Party observations for corresponding European App. No. 15791025.8 dated Oct. 27, 2017.
International Search Report dated Feb. 5, 2016, issued in corresponding International Application No. PCT/US2015/055667.
Written Opinion of the International Searching Authority dated Feb. 5, 2016, issued in corresponding International Application No. PCT/US2015/055667.
"E cigarette labeling machine" uploaded by Cherry Wang, Sep. 1, 2014 [retrieved on Feb. 1, 2016]; Retrieved from the Internet: <URL:https://www.youtube.com/watch?v=7uFodYd0xTI>. times 0:00s to 0:30s.
"Labeling machine auto labeler equipment for Electronic cigarette" uploaded by Penglai Industrial Corporation Limited, Sep. 17, 2013 [retrieved Feb. 1, 2016]: Retrieved from the Internet: <URL:https://www.youtube.com/watch?v=zKyXiOYS8_Y>. time 0:00s to 1:10s.
International Search Report dated Feb. 26, 2016, issued in corresponding International Application No. PCT/US2015/066290.
Written Opinion of the International Searching Authority dated Feb. 26, 2016, issued in corresponding International Application No. PCT/US2015/066290.
Chinese Office Action dated Sep. 17, 2018 for corresponding Chinese Application No. 201580031565.9.
Office Action for corresponding Eurasian Application No. 201791107 dated Jan. 30, 2019 and English translation.
International Search Report dated Feb. 3, 2016, issued in corresponding International Application No. PCT/IB2015/001477.
Written Opinion of the International Searching Authority dated Feb. 3, 2016, issued in corresponding International Application No. PCT/IB2015/001477.

(56) References Cited

OTHER PUBLICATIONS

U.S. Appl. No. 14/686,431, filed Apr. 14, 2014.
U.S. Appl. No. 15/869,615, filed Jan. 12, 2018.
U.S. Appl. No. 15/978,321, filed May 14, 2018.
Office Action for corresponding U.S. Appl. No. 15/869,615 dated Nov. 5, 2019.
Office Action for corresponding U.S. Appl. No. 14/686,431 dated Dec. 20, 2019.
Search Report for corresponding European Application No. 15871050.9 dated Jul. 23, 2018.
U.S. Notice of Allowance dated Feb. 12, 2020 for corresponding U.S. Appl. No. 15/869,615.
Office Action for corresponding U.S. Appl. No. 15/978,312 dated Feb. 13, 2020.
U.S. Notice of Allowance dated Mar. 26, 2020 for corresponding U.S. Appl. No. 15/978,321.
Chinese Office Action dated Jun. 5, 2019, issued in corresponding Chinese Patent Application No. 201580055337.5.
Office Action for corresponding U.S. Appl. No. 14/686,431 dated Jun. 27, 2019.

\* cited by examiner

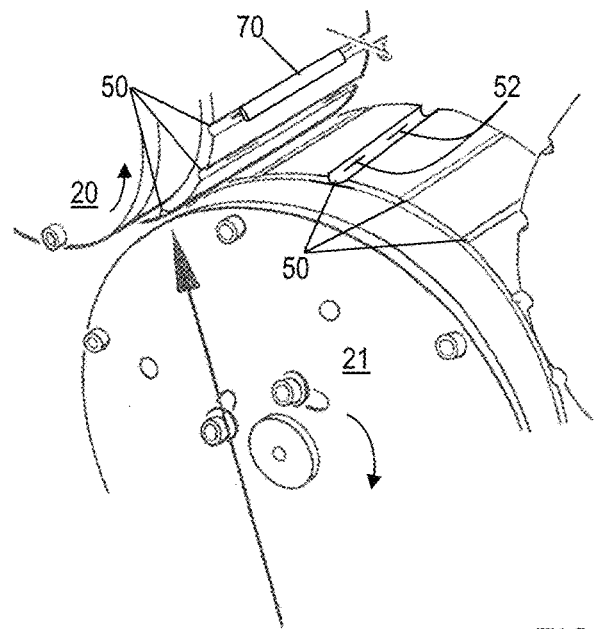
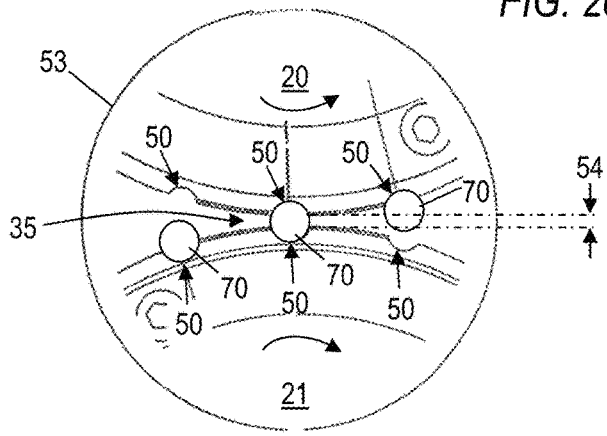
FIG. 2c
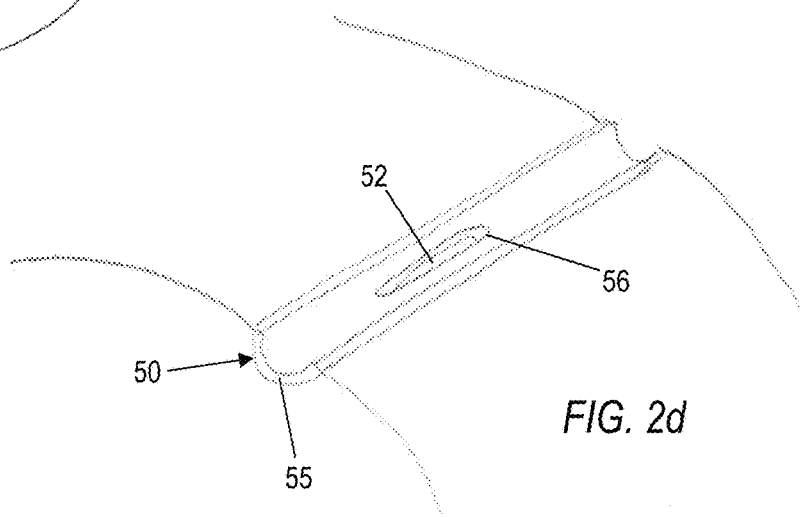
FIG. 2d

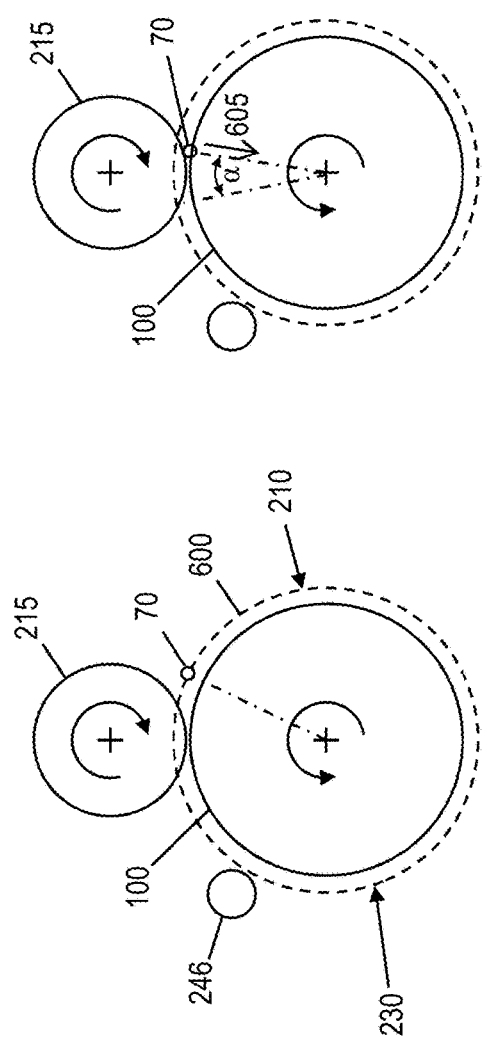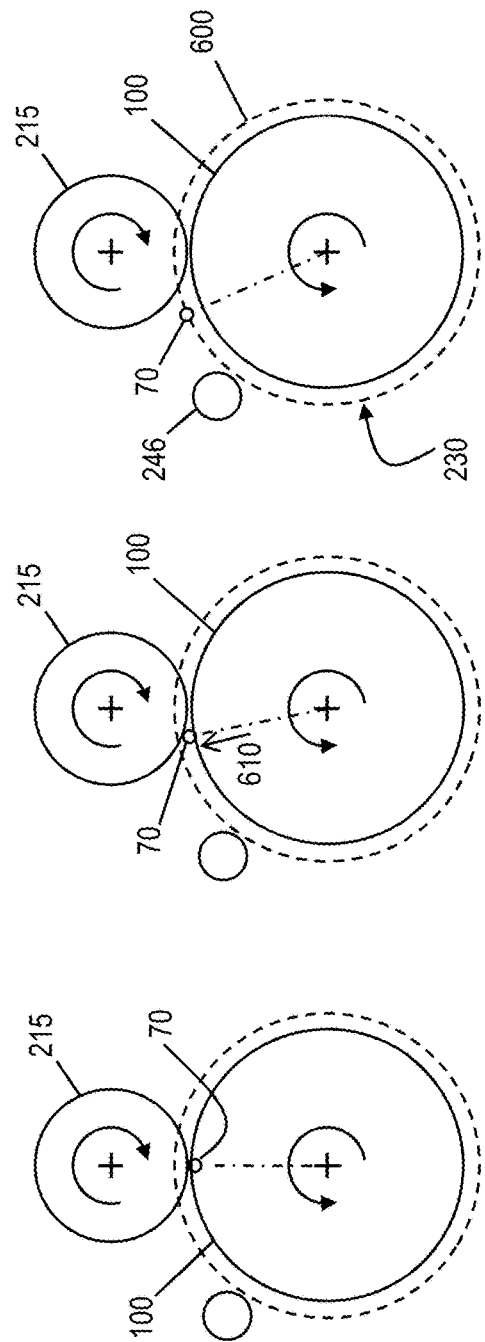

US 10,858,137 B2

SYSTEM AND METHOD FOR APPLYING A LABEL FOR THE AUTOMATED PRODUCTION OF E-VAPOR DEVICES

CROSS-REFERENCE TO RELATED APPLICATION

This application claims priority under 35 U.S.C. § 119(e) to U.S. Provisional Application No. 62/094,743, filed Dec. 19, 2014, the entire contents of which is incorporated herein by reference.

BACKGROUND

Field

This disclosure relates generally to systems and methods for manufacturing vapor-generating articles and, more particularly, to systems and methods for manufacturing electronic vaping articles.

Description of the Related Art

Electronic vapor-generating articles may be manufactured via a number of manual operations. However, such operations are not only labor intensive and time consuming but also more prone to inconsistency.

SUMMARY

Some example embodiments described herein are directed to automated manufacturing of electronic vapor-generating articles, such as electronic vapor devices, regardless of their size and shape. Aspects are directed to a labeler system for use in manufacturing electronic vapor devices. The labeler system is structured and arranged to tag (i.e., initially attach) a label to a rigid housing of an electronic vapor device, press a leading edge of the label against the housing after the tagging, and subsequently roll the label around the housing. In this manner, the labeler system is useful as an automated system for manufacturing electronic vapor devices.

In accordance with aspects disclosed herein, there is a system for use in manufacturing vapor-generating articles. The system includes a rotatable drum structured and arranged to hold at least one vapor-generating article (e.g., a plurality of the vapor-generating articles). The system also includes a tagging drum structured and arranged to tag a respective label to a housing of each of the vapor-generating articles. The system further includes a pressing roller structured and arranged to press a leading edge of the label against the housing after the tagging. The system additionally includes a rolling drum structured and arranged to roll the label around the housing after the pressing.

In accordance with additional aspects disclosed herein, there is a method of applying labels to vapor-generating articles. The method includes arranging a vapor-generating article in one or more seats on an outer surface of a rotating drum. The method also includes tagging a respective label to a housing of each of the vapor-generating articles. The method additionally includes pressing a leading edge of the label against the housing after the tagging. The method further includes rolling the label around the housing after the pressing.

In accordance with further aspects disclosed herein, there is a pressing roller used for applying labels to vapor-generating articles. The pressing roller includes a roller body arranged adjacent to a rotatable drum carrying a vapor-generating article to which a label is adhered at an intermediate location. The pressing roller also includes a plurality of flutes in an outer face of the roller body. The roller body is configured to be driven relative to the rotating drum such that one of the plurality of flutes contacts a leading edge of the label and presses the leading edge of the label against the housing.

BRIEF DESCRIPTION OF THE DRAWINGS

Various aspects are further described in the detailed description which follows, in reference to the noted plurality of drawings by way of non-limiting examples of embodiments, in which like reference numerals represent similar parts throughout the several views of the drawings.

FIGS. 2b-2d show aspects of systems and methods for the automated manufacture of electronic vapor devices using rotating drums in accordance with an example embodiment;

FIGS. 6a-6e show aspects of applying a label to an electronic vapor device in accordance with an example embodiment;

DETAILED DESCRIPTION

Figure 1A:
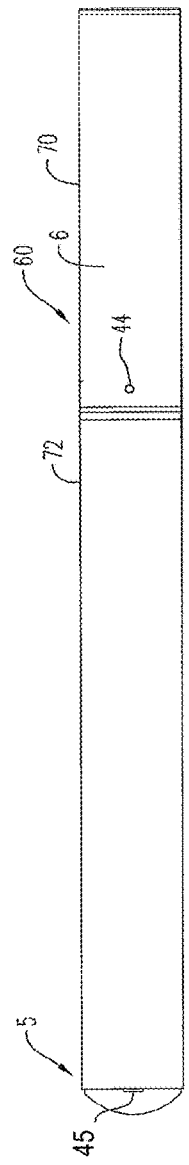
FIGS. 1a, 1b, 1c, and 1d show electronic vapor devices in accordance with various example embodiments.

Various aspects will now be described with reference to specific forms selected for purposes of illustration. It will be appreciated that the spirit and scope of the apparatus, system, and methods disclosed herein are not limited to the selected forms. Moreover, it is to be noted that the figures provided herein are not drawn to any particular proportion or scale, and that many variations can be made to the illustrated forms. Reference is now made to the figures, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems, and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Some example embodiments described herein are directed to a labeler system for use in manufacturing electronic vaping articles, although the present disclosure is not limited thereto. Various embodiments are described with reference to electronic vapor devices, but it should be understood that aspects described herein may be used with any type of electronic vaping article. The labeler system described herein may include: a rotatable/rotating drum that is configured to carry one or a plurality of partially or completely assembled electronic vaping articles; a tagging drum that is configured to tag (i.e., initially attach) a respective label to a housing of each of the electronic vaping articles; a pressing roller that is configured to press a leading edge of the label against the housing after the tagging; and a rolling drum that is configured to roll the label around the housing after the tagging and the pressing. In this manner, example embodiments are useful for applying labels to electronic vapor devices during automated manufacturing operations.

Electronic Vapor Device Layout

Figure 1B:
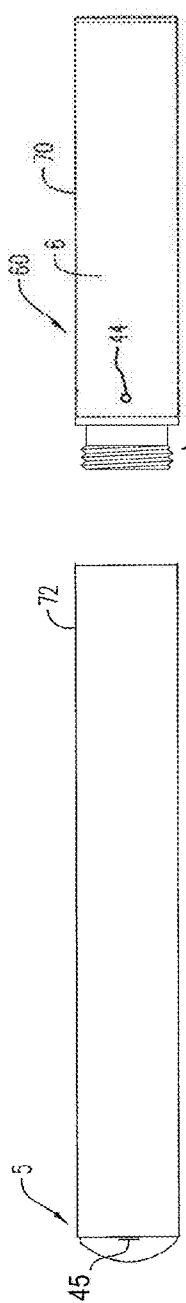

Referring to FIGS. 1a and 1b, an electronic vapor device (article) 60 is provided and comprises a replaceable cartridge (also called a first section or cartridge unit) 70 and a reusable fixture (also called a second section or battery section) 72, which in an example embodiment are coupled together at a threaded connection 205 or by other suitable arrangements such as a snug-fit, detent, clamp, and/or clasp.

Generally, the second section 72 may include a puff sensor that is responsive to air drawn into the second section 72 via an air inlet port 45 that is adjacent to the free end or tip of the electronic vapor device 60, a battery, and control circuitry. The disposable first section 70 includes a supply region and a heater that vaporizes a pre-vapor formulation that is drawn from the supply region through a wick. A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol. In a non-limiting embodiment, the supply region may be a liquid supply region that contains an e-liquid.

Figure 1C:
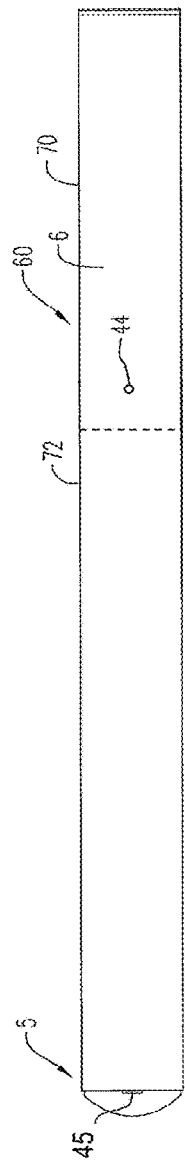
Figure 1D:
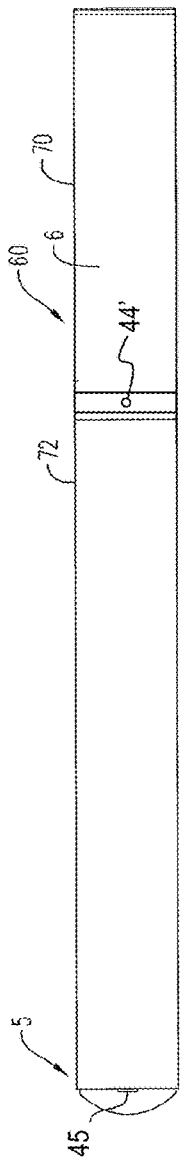

The first section 70 according to an example is a cartridge section and includes an outer housing 6 that houses the liquid supply region, heater, and wick. Upon completing the threaded connection 205, the battery of the second section 72 is connectable with the electrical heater of the first section 70 upon actuation of the puff sensor. Air is drawn primarily into the first section 70 through one or more air inlets 44 during drawing action upon the mouth end of the first section 70. The drawing action is communicated to a puff sensor in the second section 72 which causes the battery-powered heater to vaporize some of the liquid from the liquid supply region. The vaporized liquid is entrained in the air that is drawn in through the one or more air inlets 44 and delivered via one or more ports at the mouth end of the first section 70. As shown in FIG. 1d, the one or more air inlets 44' may be located at a structure associated with the threaded connection 205, including but not limited to a connector ring between the first section 70 and the second section 72.

In an example embodiment, once the liquid of the cartridge is spent, only the first section 70 is replaced. An alternate arrangement shown in FIG. 1c includes an implementation in which the first section 70 and the second section 72 are integrally attached, such that the entire electronic vapor device 60 is disposed once the liquid supply is depleted. In such case the battery type and other features might be engineered for simplicity and cost-effectiveness while generally embodying the same concepts as in an embodiment in which the second section is reused and/or recharged.

In an example embodiment, the electronic vapor device 60 may be about 80 mm to about 110 mm long (e.g., about 80 mm to about 100 mm long) and about 7 mm to about 10 mm or more in diameter. For example, in an embodiment, the electronic vapor device is about 84 mm long and has a diameter of about 7.8 mm. Implementations are not limited to these dimensions, and aspects described herein may be adapted for use with any size electronic vaping article.

At least one adhesive-backed label may be applied to the outer housing 6 of the first section 70. The label may completely circumscribe the electronic vapor device 60 and can be colored and/or textured. The label can include holes therein which are sized and positioned so as to prevent blocking of the air inlets 44.

The outer housing 6 may be formed of any suitable material or combination of materials. Examples of suitable materials include metals, alloys, plastics, paper, fiberglass (including woven fiberglass) or composite materials containing one or more of those materials, or thermoplastics that are suitable for food or pharmaceutical applications, for example polypropylene, polyetheretherketone (PEEK), ceramic, and polyethylene. The material may be light and non-brittle. In an example, the outer housing 6 is composed of metal, such as stainless steel, aluminum, or aluminum alloy.

Automated Manufacture Using Rotating Drums

FIGS. 2a-2d and 3 show aspects of systems and methods for the automated manufacture of vapor-generating articles (such as, by way of example, electronic vapor devices) using rotating drums in accordance herewith. Aspects of FIGS.

2a-2d and 3 are described with respect to automated manufacturing processes associated with the first section 70 (also referred to herein as a cartridge unit 70) of an electronic vapor device 60. The systems and methods described herein are not limited to use with the first section 70, however, and instead may be used with automated manufacturing processes associated with a second section 72 (e.g., a battery section) and/or a combined article including a connected first section 70 and second section 72.

Figure 2A:
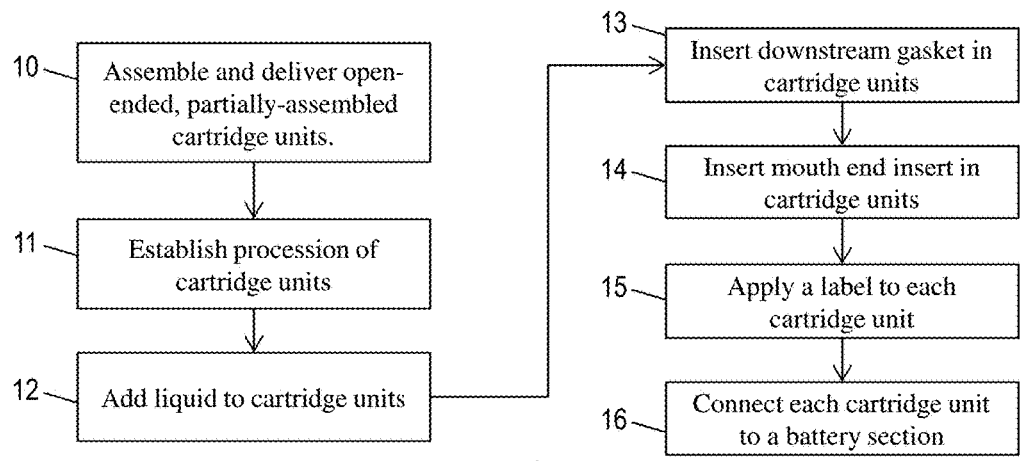
FIG. 2a is a block diagram of a process for automated assembly of electronic vapor devices in accordance with an example embodiment.

FIG. 2a is a block diagram of a process for automated assembly of electronic vapor devices in accordance with an example embodiment. In embodiments, the process includes assembling and delivering open-ended, partially-assembled cartridge units 70 (step 10); establishing a procession of the open-ended, partially-assembled cartridge units 70 (step 11); adding liquid to the liquid supply region of the cartridge units 70 (step 12); inserting a respective downstream gasket into each of the cartridge units 70 (step 13); inserting a respective mouth-end insert into each of the cartridge units 70 (step 14); applying a respective label to the outer housing of each of the cartridge units 70 (step 15); and connecting a respective battery section (i.e., second section 72) to each of the cartridge units 70 (step 16).

In aspects, the processes performed at steps 10-16 are automated, e.g., using computer-controlled manufacturing machinery. In additional aspects, the cartridge units 70 are handled and transported during and between steps 10-16 in an automated manner, e.g., using rotating drums as described herein. In even further aspects, one or more inspection processes is performed after each one of steps 10-16, e.g., to detect cartridge units 70 that are out of specification. The method is not limited to the particular steps 10-16; instead, more or less steps and/or different steps and/or a different order of steps may be used.

Figure 2B:
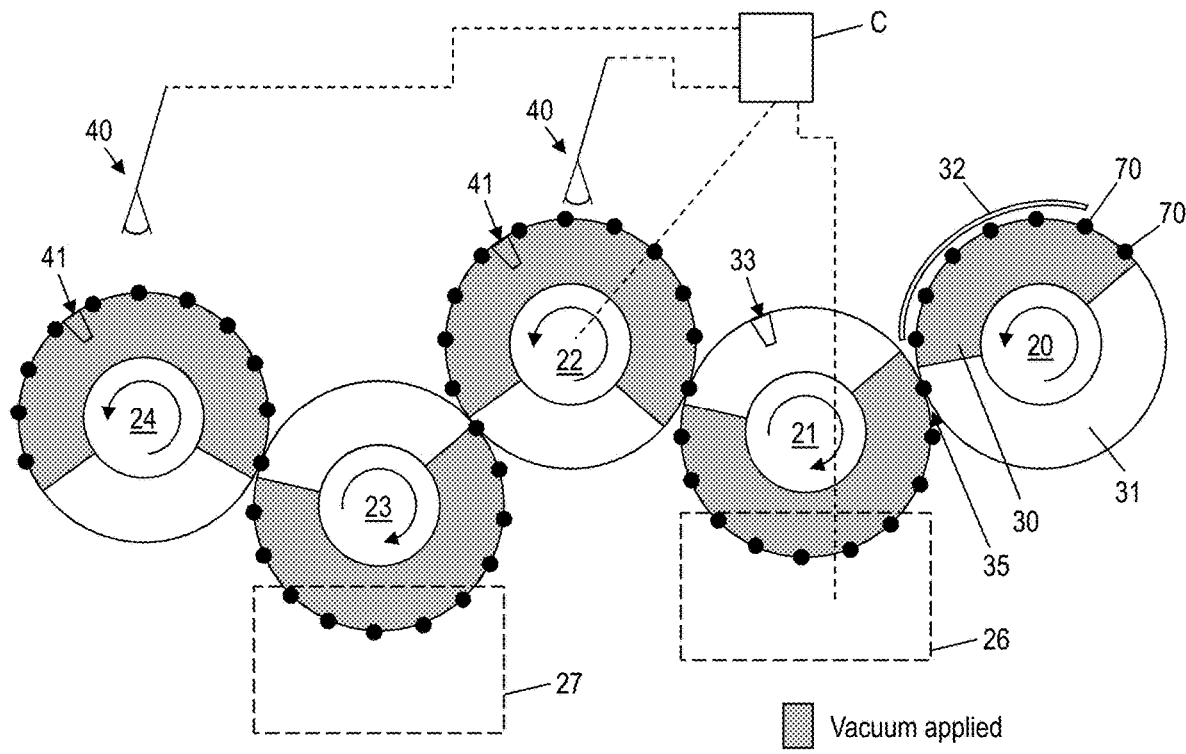

FIGS. 2b-2d depict drum-to-drum transfer systems and methods that may be used with aspects of automated assembly of electronic vapor devices in accordance herewith. Aspects shown in FIGS. 2b-2d may be used in the handling and transporting of cartridge units 70 during and between steps 11-16 described with respect to FIG. 2a, for example. As shown in FIG. 2b, a procession of a plurality of cartridge units 70 (shown individually as solid circles) may be carried by a plurality of rotating drums 20-24 to work stations 26, 27 where manufacturing/assembly processes are performed on the cartridge units 70. In aspects, the work stations 26, 27 may correspond to any of steps 11-16. In but one example, work station 26 may include machinery configured to insert a respective downstream gasket into each of the cartridge units 70, and work station 27 may include machinery configured to insert a respective mouth-end insert into each of the cartridge units 70. Although only two work stations 26, 27 are shown for simplicity, it is understood that rotating drums similar to drums 20-24 may be used to carry cartridge units 70 to other work stations during the automated manufacture of electronic vapor devices.

In example embodiments, each drum 20-24 may include a cylindrical body with a plurality of grooves (also called flutes) spaced apart on its roll face. Each flute may be structured and arranged to hold and carry a section of an electronic vapor device, such as a cartridge unit 70. As described in greater detail with respect to FIGS. 2c and 2d, each flute may include a resilient (e.g., yieldable) material that directly contacts the cartridge unit 70 when the cartridge unit 70 is held in the flute and carried by the rotating drum.

Still referring to FIG. 2b, each drum 20-24 may include a vacuum system that selectively applies a vacuum force to the flutes to assist in holding the cartridge units 70 in the flutes during rotation of the drum. For example, the system may be adapted such that during rotation of the drums 20-24, flutes that are located in shaded areas 30 are provided with a vacuum force, while flutes that are located in unshaded areas 31 are not provided with the vacuum force. Specifically, a particular flute on counterclockwise rotating drum 20 is provided with the vacuum force when the flute is moving through the shaded area 30, and is not provided with the vacuum force when the flute is moving through the unshaded area 31. The vacuum force may be selectively applied to each flute on each drum individually, such as via a vacuum port in each flute and a vacuum source internal to the drum that selectively applies a vacuum force to the vacuum port in a particular flute based on the angular position of the particular flute along the rotational path of the roll face of the drum.

Rails 32 may also be provided adjacent to one or more of the drums 20-24 to assist in maintaining the cartridge units 70 in the flutes. Furthermore, cleaning air may be communicated to the port(s) of each flute at angular positions such as that indicated by area 33. The cleaning air may be selectively applied to each flute individually.

In aspects, when transferring a cartridge unit 70 from a donating flute of a first drum to a receiving flute of a second drum, e.g., from drum 20 to drum 21, a vacuum force is deactivated at the donating flute when the donating flute is at a location prior to the nip 35 between the first drum and the second drum. Also, a vacuum force is activated at the receiving flute when the receiving flute is at a location prior to the nip 35 between the first drum and the second drum. This coordination of the timing of the respective vacuum forces applied at the donating flute and the receiving flute is depicted by shaded areas 30 and unshaded areas 31 in FIG. 2b and facilitates moving the cartridge unit 70 out of the donating flute and into the receiving flute.

With continued reference to FIG. 2b, the system may include a controller "C" that is operatively connected to one or more elements. As described herein, the controller "C" may be a computer-based controller that employs hardware and software to perform automated control processes. For example, the controller "C" may be operatively connected to one or more detectors 40 for the purpose of inspecting and/or tracking cartridge units 70 during the automated manufacturing. The detectors 40 may comprise cameras or other optical detecting mechanisms that detect optical characteristics and/or information of the cartridge units 70 and transmit the detected optical characteristics and/or information to the controller 'C'.

For inspection purposes, the controller "C" may determine whether a cartridge unit 70 is out of specification, e.g., not properly assembled, damaged, etc., by comparing the detected optical characteristics to predefined optical criteria. Any cartridge unit 70 that is determined to be out of specification based on the detecting may be ejected from one of the rotating drums, e.g., by selectively disabling the vacuum of a flute carrying the out of specification cartridge unit and/or applying a jet of air to the flute, e.g., as indicated at location 41, to eject the cartridge unit 70 from the flute. It is envisioned that an inspection station may be located downstream of the ejection station 41, to confirm proper operation of the ejection station 41. The controller "C" may be programmed to track any empty flute position resulting from an ejection, and to track the empty flute position through the system (e.g., the entire system or to the next downstream workstation).

Alternatively or in addition, for tracking purposes, each cartridge unit 70 may be encoded with information such as:

date of manufacture, unique tracking identification, authentication, lot number, facility identification, and model number. More specifically, the individual cartridge units 70 may be printed with indicia that provide such information. The detectors 40 may include a device, such as a camera or bar code reader, which reads the encoded information on each of the cartridge units as the cartridge units are moved by the drums 20-24. The controller "C" may be programmed to track the position of each cartridge unit 70 in the system based on the encoded information detected by the detectors 40.

As depicted in FIG. 2b, the controller "C" may also be operatively connected to the drums 20-24, for example, to control the rotational speed of each drum. The controller "C" may also be operatively connected to the work stations 26, 27, for example, to control aspects of the automated processes that are performed at the stations.

FIGS. 2c and 2d show aspects of the flutes and drums as described herein. In embodiments, the flutes 50 that receive and carry the cartridge units 70 are embodied as grooves or channels at the outer surface (e.g., roll face) of the rotatable/rotating drums (e.g., drums 20-24). As shown in FIG. 2c, in aspects herein, the longitudinal axis of the cartridge unit 70 is transverse to the direction of rotation of the drum when the cartridge unit 70 is seated in the flute 50. Each flute 50 may include at least one port 52 that is in communication with a vacuum/pressure source of the drum. Depending on the angular location of the flute 50 along the rotational path of the drum, the vacuum/pressure source of the drum may selectively apply a vacuum, an air jet, or no force at the port 52, e.g., as described with respect to areas 30, 31, and 33 of FIG. 2b.

As shown in the magnified portion 53 of FIG. 2c, in embodiments there is a clearance 54 between the roll surfaces of the respective drums (e.g., drums 20 and 21) at the nip 35 between the drums. For example, when the cartridge unit 70 has an outside diameter of about 7.8 mm, the clearance 54 may be about 0.5 mm to about 1 mm, although any suitable dimension of clearance may be used.

As shown in FIG. 2d, the surface of each flute 50 may be coated or covered with a resilient (e.g., yieldable) material 55. An opening 56 in the resilient material 55 aligns with the port 52 such that vacuum or an air jet may be applied to the flute via the port 52 and opening 56. The resilient material 55 may be applied to surfaces of the drum outside of the flutes 50, for example, over the entire roll face of the drum. In another embodiment, the entire drum (e.g., drums 20-24) may be constructed of the resilient material 55. In another embodiment, the resilient material 55 is provided over less than the entire flute 50; for example, a seat of resilient material may be provided in a sub-section of a flute. Such a resilient material 55 may be used with any type of drum based on the system requirements, including but not limited to a wrapping drum, MR drum, roll hand, etc.

In accordance with aspects herein, the resilient material 55 comprises a material that is softer (i.e., has a lower hardness) than the material of the outer housing 6 of the cartridge unit 70. For example, in an embodiment, the outer housing 6 may be composed of a metal or metal alloy and the resilient material 55 may be composed of a plastic or rubber material. In an embodiment, the outer housing 6 is composed of stainless steel or an aluminum alloy, and the resilient material 55 is composed of polyoxymethylene (POM, Delrin, etc.), although example embodiments are not limited to these materials and any suitable materials may be used.

The resilient material 55 facilitates handling the cartridge units 70 during the speeds that are involved with the rotating drums during the automated manufacture of electronic vapor devices 60 as described herein. In particular, the yieldable nature of the resilient material 55 promotes a more complete seal of the cartridge unit 70 at the vacuum port in a flute, which enhances the vacuum retention force applied to the cartridge unit 70 in the flute. Such arrangement assures retention of articles on the flutes even at higher production speeds and/or with heavier, larger articles.

Labeler System

Figure 3:
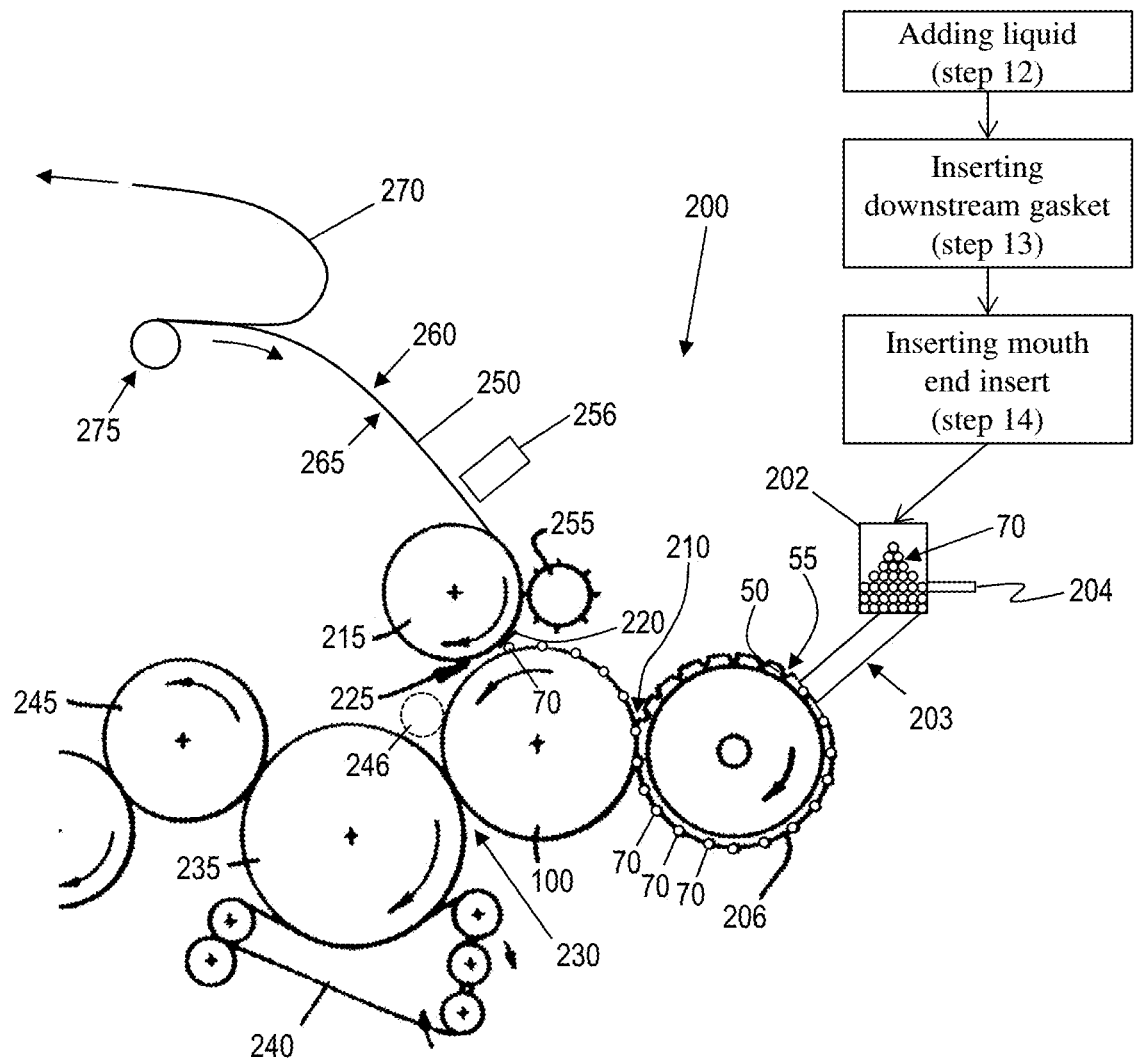
FIG. 3 shows aspects of an automated system for applying a label to an electronic vapor device in accordance with an example embodiment.

FIG. 3 shows aspects of a labeler system 200 for the automated applying of labels to electronic vapor devices in accordance with an example embodiment. The system 200 may be, for example, part of a tipping machine utilized in the manufacture of electronic vapor devices, such as electronic vapor device 60. As described herein, a label or wrapper may be applied to the exterior surface of the housing 6 of the first section (i.e., cartridge unit) 70 to provide a desired aesthetic appearance and/or tactile feel to the electronic vapor device 60. The system 200 may be part of an automated assembly path as disclosed in U.S. Application No. 61/979,326, filed Apr. 14, 2014, the entire contents of which are expressly incorporated herein by reference. In addition, the system may include aspects of machinery described in U.S. Application No. 61/979,330, filed Apr. 14, 2014 and/or U.S. Pat. No. 5,024,242, the entire contents of both of which are expressly incorporated herein by reference.

In example embodiments, the system 200 may be used to perform step 15 as described with respect to FIG. 2a. In such an implementation, the system 200 may include an accumulator 202 that receives and holds a plurality of cartridge units 70 after they have undergone processing of steps 12-14 as described with respect to FIG. 2a. The accumulator 202 functions as a buffer between the machinery that performs step 14 and that of step 15. The accumulator 202 may comprise, for example, a zig-zag or S-shaped pathway through which the cartridge units 70 travel between an accumulator inlet and an accumulator outlet 203. The accumulator inlet may be vertically higher than the accumulator outlet 203 such that the cartridge units 70 travel through the accumulator via gravity. The accumulator 202 may be sized to receive cartridge units at the accumulator inlet at a faster rate than cartridge units are released at the accumulator outlet 203. In this manner, the accumulator 202 provides a buffer that compensates for empty slots in the procession, e.g., cartridge units that were ejected from the procession based on the inspection step or missing in the procession as a result of inconsistent loading.

A sensor 204, such as a photo eye or similar, may be arranged at the accumulator 202 to determine whether the amount of cartridge units 70 in the accumulator 202 exceeds a threshold. The sensor 204 may be operatively connected to a controller of the system 200. When the sensor 204 communicates to the controller that the level of cartridge units 70 in the accumulator 202 falls below the threshold, the controller may temporarily stop the drums downstream of the accumulator 202, i.e., to pause the labeling operation. This pausing permits cartridge units 70 to accumulate in the accumulator 202 since the upstream equipment may continue to process and deliver cartridge units 70 to the accumulator 202. The sensor 204 detects when a sufficient number of cartridge units 70 has accumulated in the accumulator 202 (i.e., exceeds the threshold), at which time the controller, based on the signal from the sensor 204, automatically re-starts the drums of system 200 to resume the labeling operation.

In example embodiments, a transfer drum 206 with flutes 50 around its outer perimeter receives cartridge units 70 from the accumulator outlet 203. The transfer drum 206 may be similar to the drums 20-24 described with respect to FIG. 2b. For example, each flute 50 of the transfer drum 206 is sized to receive a single cartridge unit 70. Each flute may also be provided with a resilient material 55 for contacting the cartridge unit 70. Each flute 50 may also have at least one aperture (such as port 52 and opening 56) that is configured to selectively communicate a vacuum force to a cartridge unit seated in the flute 50, i.e., for keeping the cartridge unit 70 seated in the flute 50.

In example embodiments, the system is arranged such that rotation of the drum 206 moves an empty flute 50 past and under the accumulator outlet 203. Gravity pulls a cartridge unit 70 at the accumulator outlet 203 into the empty flute 50. In addition to or alternatively to gravity, air pressure and/or a positive force applied by a wheel or belt may be used to move the cartridge unit 70 at the accumulator outlet 203 into the empty flute 50. Vacuum may also be selectively applied to the flute 50 to assist in pulling the cartridge unit 70 from the accumulator outlet 203 into the empty flute 50. As the drum 206 continues to rotate, the trailing wall of the flute 50 strips the cartridge unit 70 from the accumulator outlet 203. Vacuum may be selectively applied to the flute 50 to maintain the cartridge unit 70 in the flute 50 until rotation of the drum 206 brings the cartridge unit to the next rotating drum 100.

At location 210, the cartridge units 70 are transferred from the transfer drum 206 to a drum 100, which rotates in a direction opposite the rotation of the drum 206. Each cartridge unit 70 is held in a respective seat 115 on the drum 100 as described in greater detail herein with respect to FIGS. 4, 5a, and 5b. A tagging drum 215 is situated adjacent drum 100 and rotates in a clockwise direction. In example embodiments, the tagging drum 215 carries a plurality of labels 220 and tags a respective label 220 to a respective cartridge unit 70 at location 225.

At location 230, each cartridge unit 70 with its associated label 220 is transferred from the drum 100 to a rolling drum 235, which rotates in a clockwise direction. Rolling drum 235 conveys each cartridge unit 70 and its associated label 220 into contact with belt 240. The belt 240 moves in a same direction as an adjacent portion of the surface of the rolling drum 235 but at a slightly slower speed than the rotation of the rolling drum 235, the speed difference between the belt 240 and the rolling drum 235 causing the cartridge unit 70 to rotate in a direction that causes label 220 to wrap itself around the exterior surface of the cartridge unit 70. After the wrapping operation, the labeled cartridge units 70 are transferred from the rolling drum 235 to a downstream transfer drum 245 for transfer to another station for further processing, such as connecting the cartridge unit 70 to a second section 72 (e.g., as described at step 16 of FIG. 2a).

In example embodiments, an additional pressing roller 246 may be provided adjacent to drum 100 at a location after the label is tagged to the cartridge unit 70 and before the cartridge unit 70 is transferred to the rolling drum 235. The pressing roller 246 may be structured and arranged to press an unsecured leading edge 305 (shown in FIG. 5a) of the label 220 to the outer surface of the cartridge unit 70 prior to the cartridge unit 70 being passed to the rolling drum 235, as described in greater detail herein with respect to FIGS. 7 and 8.

The transfer of the cartridge units 70 from one drum to another in system 200 may be achieved using drum-to-drum transfer techniques described with respect to FIGS. 2b-d.

The flutes of one or more of the drums in the system 200 may be provided with a resilient material 55 such as that described with respect to FIGS. 2c-d to facilitate safe and consistent handling of the cartridge units 70 during high-speed rotation of the drums.

As described herein, the tagging drum 215 and the cutter 255 may be part of a tagging system that is structured and arranged to attach a label 220 to a cartridge unit 70 held in seat 115. As described herein, the rolling drum 235 and belt 240 may be part of a wrapping system that is structured and arranged to wrap the label 220 around the cartridge unit 70.

Still referring to FIG. 3, in aspects described herein the label 220 may be an individual piece of paper or the like that is cut from a continuous web 250. For example, a rotating cutter 255 or the like may cut the continuous web 250 into discrete labels 220 that are held to the surface of tagging drum 215 by a vacuum. A heater 256, such as a hot air blower, heat plate, radiative element, etc., may be used to heat the web 250 to increase the tackiness of the adhesive prior to tagging.

In example embodiments, a first side 260 of the continuous web 250 has a pressure sensitive adhesive thereon, and a second side 265 of the continuous web 250 has no adhesive. In an embodiment, the pressure sensitive adhesive is pre-applied to the continuous web 250 and covered with a backing sheet 270. For example, the continuous web 250 may be provided by a spool 275 with the adhesive and backing sheet 270 already thereon. The system 200 may be structured and arranged to unwind the continuous web 250 from the spool 275 and then peel the backing sheet 270 from the continuous web 250 to expose the pre-applied adhesive prior to the continuous web 250 coming into contact with the tagging drum 215. The separated backing sheet 270 may be moved away from the continuous web 250 using an air blower or the like. In embodiments, the spool 275 is fixed to an E-shaft, and the RPM of the E-shaft may be controlled (e.g., selectively varied) to register (e.g., align) a printed logo on a label with a position on the cartridge unit 70 via an eye.

The use of a pre-applied pressure sensitive adhesive (e.g., a peel-and-stick adhesive) on labels 220 provides an advantage over tipping machines that apply an adhesive or a solvent to the tipping paper. In particular, the application of an adhesive or a solvent to the tipping paper requires a transient time at startup of the tipping machine during which some tags are not useable. This leads to waste. The pre-applied pressure sensitive adhesive used in aspects described herein, however, does not require such a transient time during startup, and thus reduces waste. Implementations as described herein can pause in the process of wrapping articles and restart with no loss of product; program stops (e.g., due to upstream equipment) will fully utilize labeling.

Figure 4:
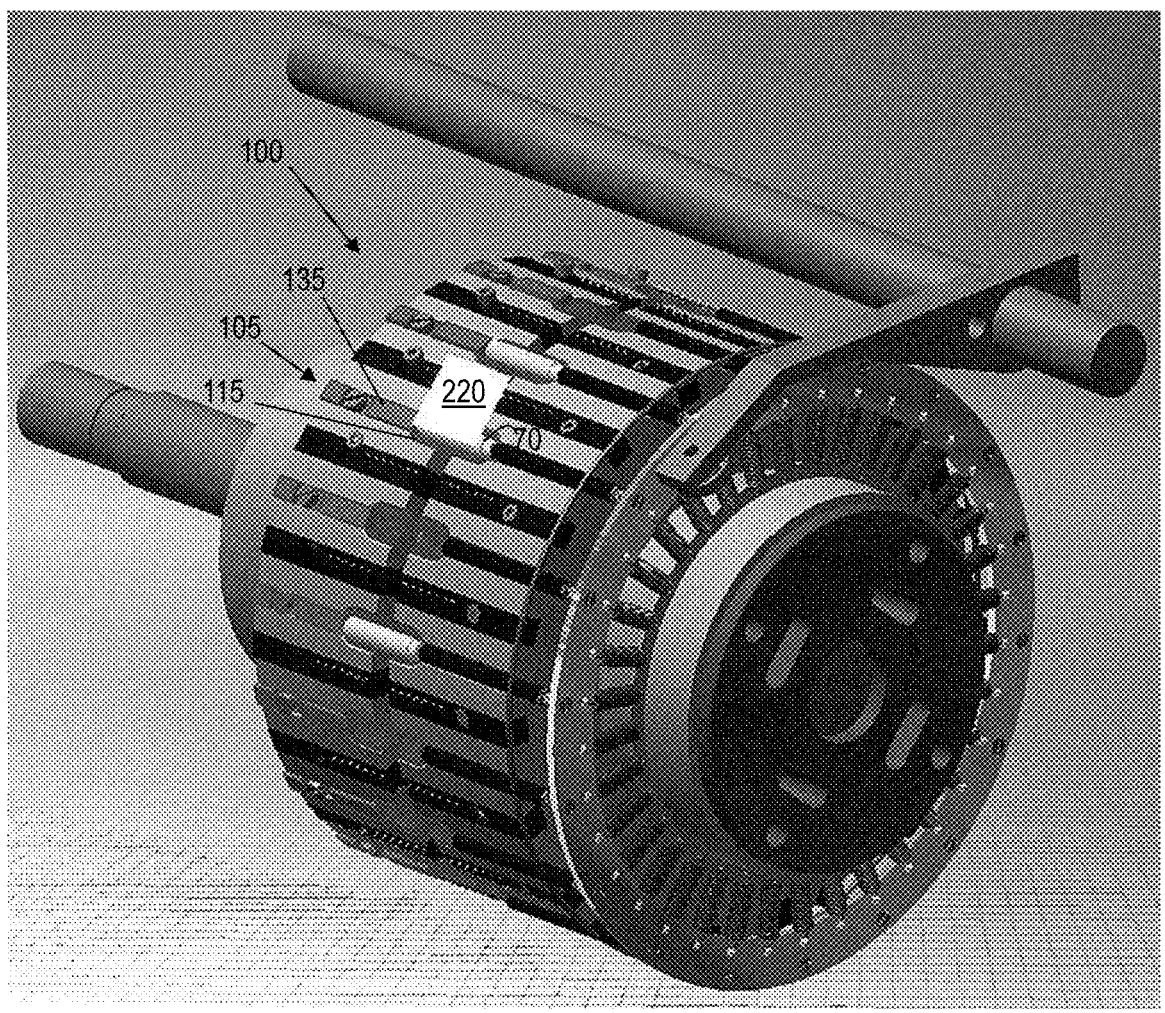
FIGS. 4 and 5a show aspects of applying a label to an electronic vapor device in accordance with an example embodiment.
Figure 5A:
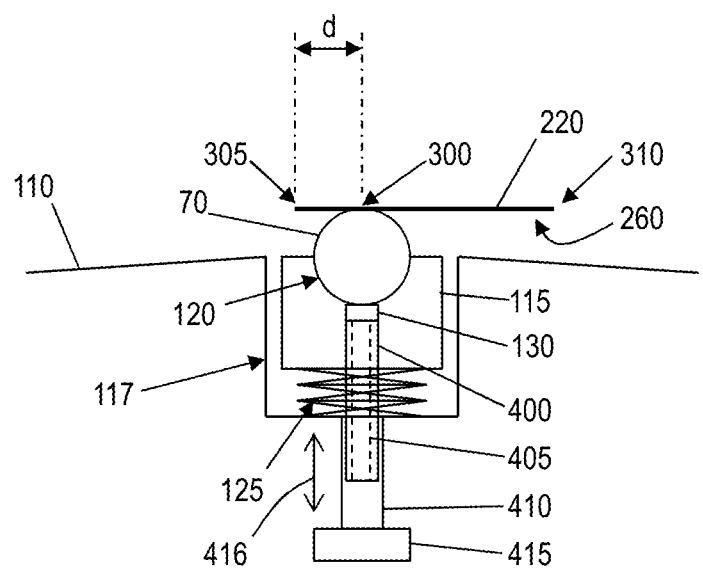

FIGS. 4 and 5a show aspects of applying a label 220 to a housing 6 of a cartridge unit 70 in accordance herewith. As shown in FIGS. 4 and 5a, drum 100 includes a cylindrical body with a plurality of flutes 105 (e.g., pockets, groove, etc.) spaced apart across its roll face 110. The drum 100, including the roll face 110 and the interior surfaces of the flutes 105, may be composed of suitable material, including but not limited to a metal or metal alloy such as steel. In embodiments, a seat 115 is located in a pocket 117 of each flute 105, and each seat 115 includes a seat groove 120 that is sized and shaped to hold a cartridge unit 70.

As shown in FIGS. 4 and 5a, a cartridge unit 70 is held in a seat 115 in drum 100 when the tagging drum 215 brings the first side 260 (e.g., the adhesive side) of the label 220 into contact with the exterior surface of the cartridge unit 70, e.g., at location 225 of FIG. 3. In embodiments, the rotation of the tagging drum 215 and the drum 100 are controlled such that an intermediate location 300 of the label 220 contacts the cartridge unit 70. More specifically, in an embodiment, the intermediate location 300 is between the leading edge 305 of the label 220 and the trailing edge 310 of the label 220, and closer to the leading edge 305 than the trailing edge 310.

As shown in FIG. 5a, the contact location at the intermediate location 300 is a length "d" away from the leading edge 305. In an embodiment, the length "d" is about 1-2 mm, although other lengths may be suitable. Making the contact point at an intermediate location 300 instead of the leading edge 305 yields improved tagging and rolling of the label 220 on the relatively hard and unyielding outer surface of the cartridge unit 70 (that is constructed, for example, of stainless steel or aluminum alloy) as compared to a tagging operation on a structure that has a relatively soft outer surface (that is constructed, for example, of paper, filter material, or the like) that yields at the locus of application during the tagging process.

With continued reference to FIG. 5a, the seat 115 may include or be connected to a post 400 having an internal channel 405. A first end of the channel 405 communicates with the hole 130 for providing vacuum force at the seat. A second end of the channel 405, opposite the first end, communicates with another channel 410 that is formed in the drum 100 and which is in communication with a vacuum source 415 associated with the drum 100. In this manner, the vacuum source 415 associated with the drum 100 may be used to selectively apply vacuum force at the seat via the channel 405 and hole 130. In a non-limiting implementation, the post 400 and channel 405 are embodied as a hollow cylindrical tube, although any suitable shape may be used.

In example embodiments, the post 400 is configured to be axially moveable inside the channel 410 as indicated by arrow 416. In aspects, the post 400 is sized relative to the channel 410 such that the lower end of the post 400 remains the channel 410 through the entire range of motion of the seat 115. In this manner, vacuum may be maintained at the seat 115 when the seat 115 moves axially against the spring 125.

In aspects, the post 400 may be located inside the spring 125. For example, the spring 125 may have the shape of a helical spring, and the post 400 may be centrally located within the spring and substantially coaxial with a longitudinal axis of the spring. More than one post 400 and spring 125 may be used for each seat 155.

Figure 5B:
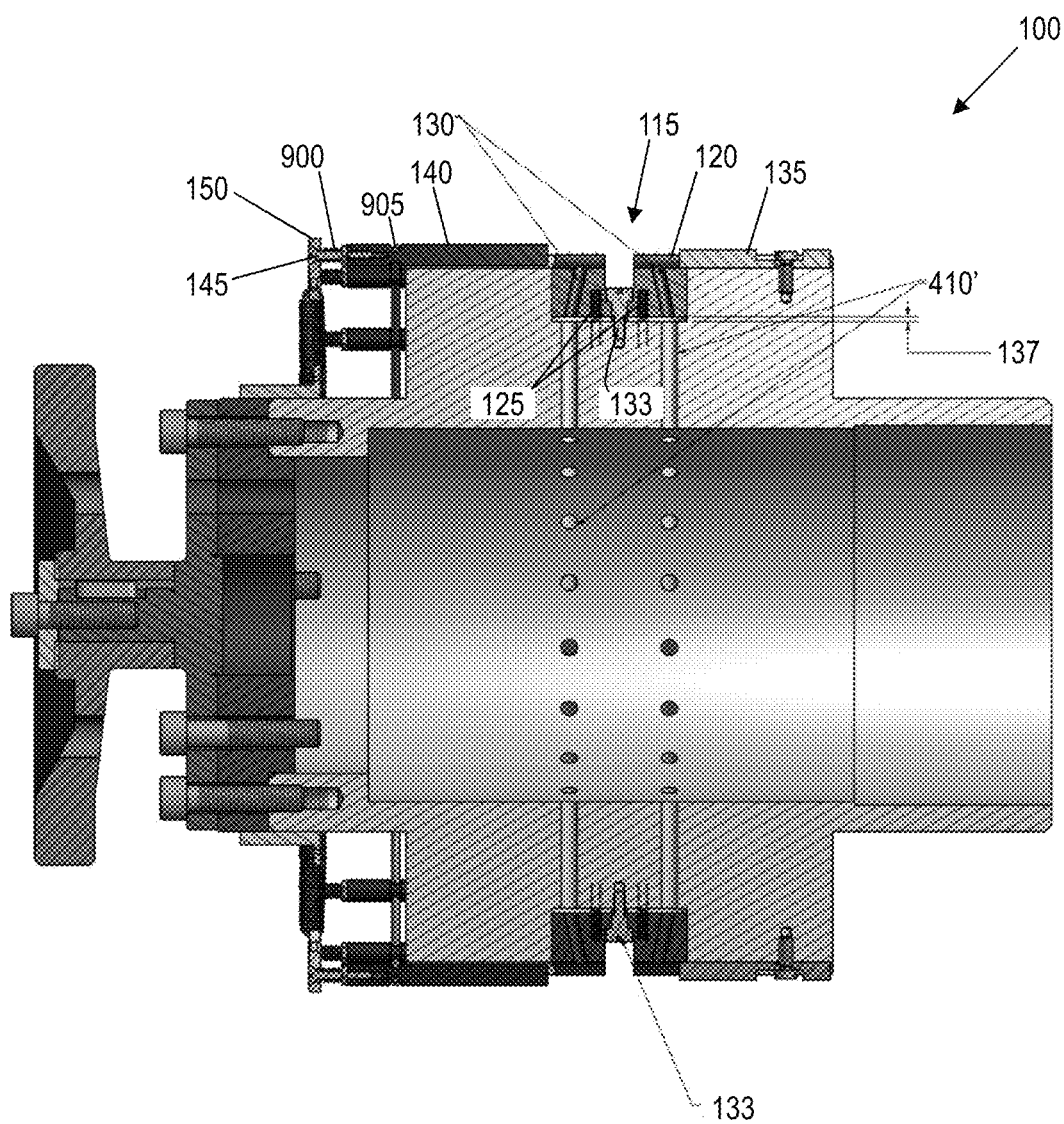
FIG. 5b shows aspects of a drum in accordance with an example embodiment.

FIG. 5b shows a cross section of an implementation of drum 100 of FIG. 3. As shown in FIG. 5b, the drum 100 includes a seat 115 with a seat groove 120 that is sized to hold a cartridge unit 70. As described herein, a swash plate 150 and a pusher 140 may be arranged to selectively push a cartridge unit 70 against the stop 135 during a label tagging process. In embodiments, a screw 145 is threaded into the end of the pusher 140, with the screw 145 extending through a hole in the swash plate 150 without being threadedly engaged to the swash plate 150. In aspects, a spring 900 surrounds the screw 145 and contacts the pusher 140 and the swash plate 150. In operation, a cam follower or similar mechanism pushes a portion of the swash plate 150 inward, which applies an axial force to the spring 900 and the pusher 140 that, in turn, exerts an axial force on a cartridge unit 70 in the seat 115. The elements of the system may be structured and arranged such that the axial force applied against the cartridge unit 70 in this manner is sufficient to hold the cartridge unit 70 against the stop 135 and prevent the cartridge unit 70 from rotating in the seat 115 when the label is applied to the cartridge unit 70. The spring 900 advantageously prevents binding during this pushing operation so that the pusher 140 will not damage the cartridge unit 70 during the pushing. In embodiments, one or more circumferential springs 905 may be arranged around the pushers 140 to prevent the pushers 140 from pivoting out of the respective flutes of the drum.

With continued reference to FIG. 5b, the limit stop structure 133 may comprise a shoulder bolt or the like. The extent of travel 137 of the seat 115 relative to the body of the drum 100 may be set to any desired value (e.g., up to 1.5 mm or similar value) by raising or lowering the cutting drum assembly, which may be regarded as comprising the tagging drum 215 and the cutter 255 (see FIG. 3).

As described herein, the seat 115 may include vacuum holes 130 that are in communication with a vacuum source in the body of the drum 100. As shown in FIG. 5b, the vacuum holes 130 may be offset from (e.g., not coincident) with the springs 125. The vacuum holes 130 may be in communication with vacuum holes 410' in the body of the drum 100 and thus used to selectively apply vacuum force at the seat groove 120 for retaining a cartridge unit 70 in the seat groove 120.

FIGS. 6a-6e show aspects of applying a label to an electronic vapor device in accordance herewith. In embodiments, the drum 100 and tagging drum 215 are sized and located relative to one another such that the tagging drum 215 causes the seat 115 to move along a radial direction of the drum 100 when the tagging drum 215 and/or a label 220 on the tagging drum 215 comes into contact with a cartridge unit 70 carried in the seat 115. As shown in FIG. 6a, the cartridge unit 70 is received in a seat 115 on the drum 100 at nip location 210 and moves along a circular path 600 toward the tagging drum 215 as the drum 100 rotates. In the location shown in FIG. 6a, the cartridge unit 70 does not yet have a label 220 tagged on its outer surface. As shown in FIG. 6b, during continued rotation of the drum 100, the cartridge unit 70 comes into contact with the label on the tagging drum 215 which moves (pushes) the cartridge unit 70 and seat 115 radially inward relative to the drum 100 as depicted by arrow 605. The spring 125 permits the seat 115 and the cartridge unit 70 thereon to be moved radially inward.

As shown in FIG. 6c, during continued rotation of the drum 100, the tagging drum 215 continues to move the cartridge unit 70 and seat 115 radially inward until the cartridge unit 70 reaches a bottom dead center position. As shown in FIG. 6d, during continued rotation of the drum 100, after passing the bottom dead center position, the spring 125 urges the seat 115 (and thus the cartridge unit 70) radially outward relative to the drum 100 as depicted by arrow 610. As shown in FIG. 6e, during continued rotation of the drum 100, the spring 125 continues to urge the seat 115 and the cartridge unit 70 radially outward until the cartridge unit 70 is once again on circular path 600 and is no longer acted upon by the tagging drum 215. In the location shown in FIG. 6e, the cartridge unit 70 has a label 220 tagged (e.g., initially adhered) on its outer surface in the manner shown in FIG. 5a. From the position shown in FIG. 6e, the drum 100 rotates the seat 115 and the cartridge unit 70 past the pressing roller 246 and then to the nip location 230 where the tagged cartridge unit 70 is transferred to the rolling drum 235.

The sizing and spacing of the drum 100 and the tagging drum 215, and the movement of the seat 115 and cartridge unit 70, as described with respect to FIGS. 6a-6e facilitates consistent and repeatable tagging (i.e., initially attaching) of labels 220 to the exterior surface of the cartridge units 70. Specifically, the movement of the seat 115 along the radial direction of the drum 100 causes the tagging drum 215 to maintain the label 220 in contact with the cartridge unit 70 throughout an included angle of rotation a of the drum 100 without damaging the relatively hard housing of the cartridge unit 70. Maintaining the label 220 in contact with the cartridge unit 70 through the included angle of rotation in this manner increases the likelihood that the label 220 is successfully tagged to the cartridge unit 70 despite possible slight misalignments of the label 220 on the tagging drum 215 relative to the cartridge unit 70 on the drum 100. The included angle α may be about 4 degrees, although other angles may be used.

Rotary Label Tucker

Figure 7:
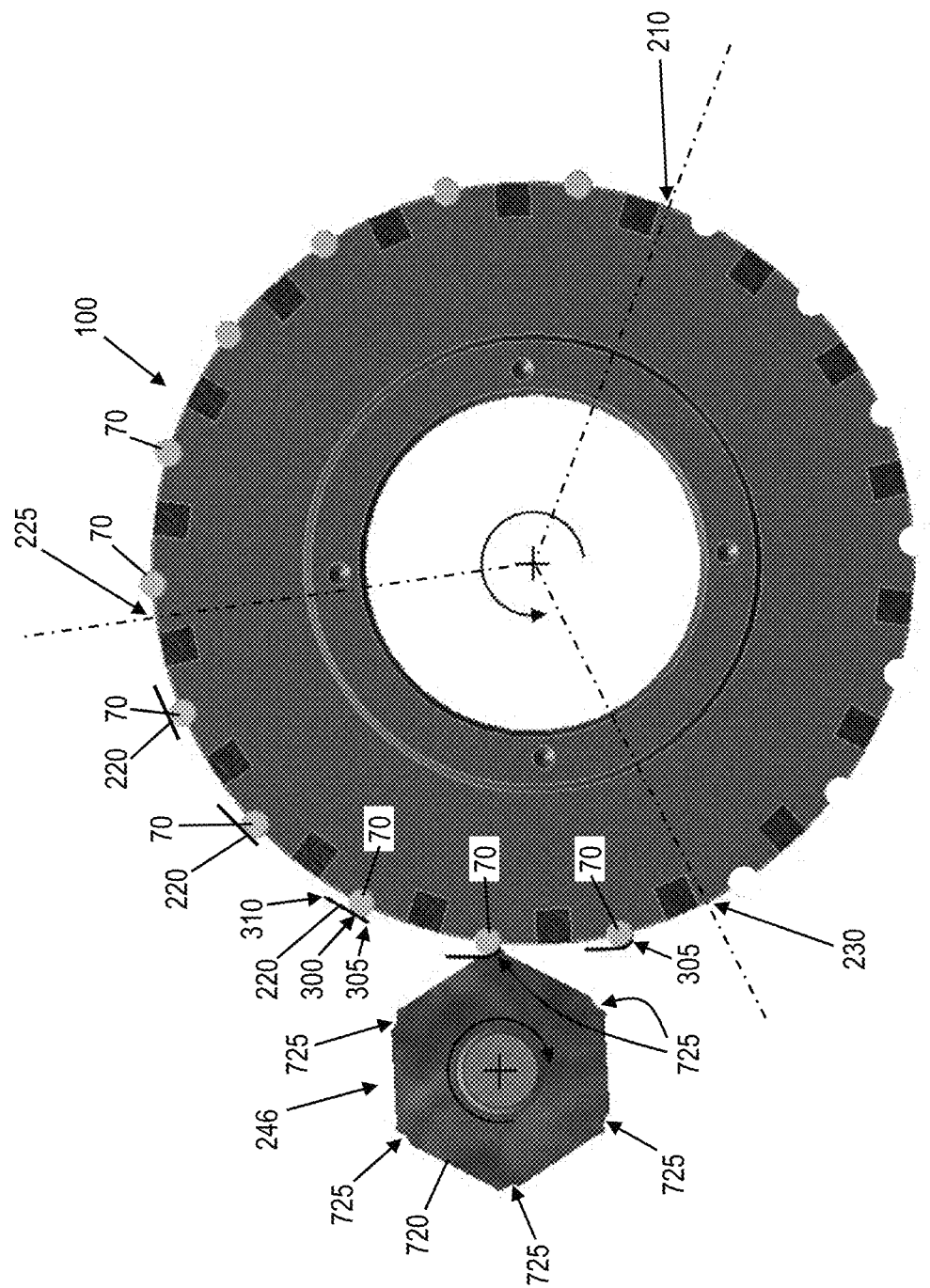
FIGS. 7 and 8 show aspects of tucking an edge of a tagged label in accordance with an example embodiment.
Figure 8:
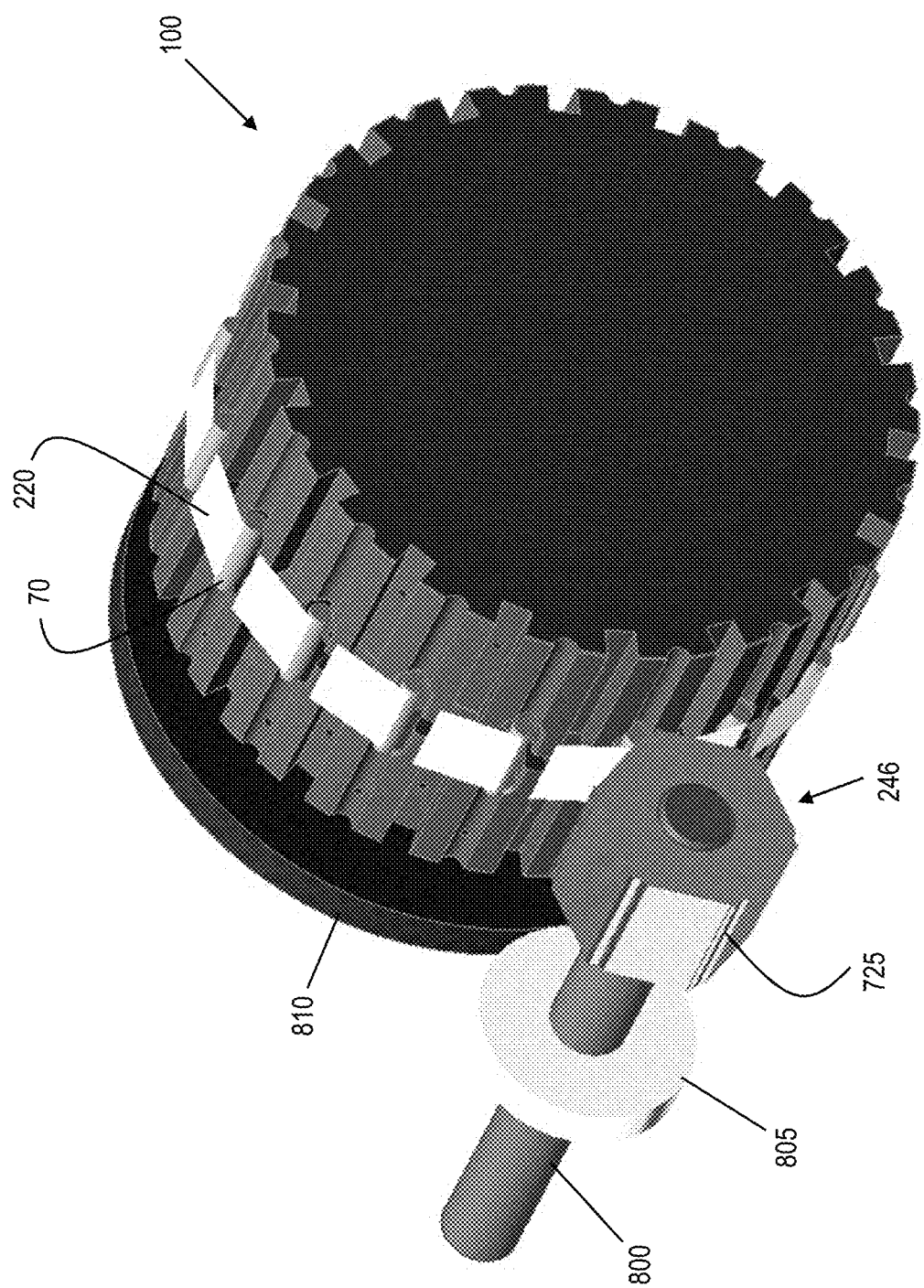

FIGS. 7 and 8 show aspects of tucking a leading edge of an already-tagged label in accordance herewith. As described with respect to FIG. 5a, and as shown in FIG. 7, the leading edge 305 of the label 220 is not attached to (devoid of contact with) the cartridge unit 70 when the label 70 is first tagged to the cartridge unit 70 at the tagging drum 215. Specifically, the label 220 initially contacts and adheres to the cartridge unit 70 only at an intermediate location 300 of the label 220 between the label leading edge 305 and the label trailing edge 310. The housing of the cartridge unit 70 is a relatively rigid material that permits only a very small area of contact of the label 220 to the cartridge unit 70 when the label is initially attached (i.e., tagged) to the cartridge unit 70, as opposed to structures that are relatively soft and are slightly deformed to form a large flat area of contact for the label during the label tagging operation. Because the relatively rigid housing of the cartridge unit 70 permits only a small contact area for the label 220, it is relatively difficult to adhere the leading edge 305 of the label 220 to the cartridge unit 70 during the tagging, e.g., since even a slight misalignment of the label 220 relative to the cartridge unit 70 could cause the leading edge 305 to fail to come into contact with the cartridge unit 70 during the tagging. Therefore, in example embodiments, the label 220 is tagged (initially adhered) to the cartridge unit 70 at the intermediate location 300 between the leading edge 305 and the trailing edge 310 to increase the likelihood that the label 220 is successfully tagged to the cartridge unit 70.

Due to the label 220 being tagged to the cartridge unit 70 at the intermediate location 300, the leading edge 305 of the label 220 is unattached to the cartridge unit 70 while the cartridge unit 70 is carried on the drum 100 toward the rolling drum 235. The unattached leading edge 305 can lead to unlabeled or improperly labeled cartridge units 70. For example, at high machine speeds (e.g., high rotational speeds of drum 100), air acting on the underside of the unattached leading edge 305 can peel (e.g., detach) the label 220 from the cartridge unit 70. This disadvantageously results in an unlabeled product that must be rejected. In another example, the distance "d" shown in FIG. 5a may exceed a desired amount which can result in the unattached leading edge 305 being folded back upon itself by the belt 240 associated with the rolling drum 235. This disadvantageously results in an improperly labeled product that must be rejected. Accordingly, implementations described herein press the leading edge 305 of the label 220 into contact with the housing of the cartridge unit 70 prior to the cartridge unit 70 being transferred from the drum 100 to the rolling drum 235. This pressing adheres the leading edge 305 to the cartridge unit 70 prior to the rolling operation at the rolling drum 235 and improves the repeatability and yield of the labeling process.

Specifically, as shown in FIG. 7, a pressing roller 246 (also called a rotary tucker) is structured and arranged to urge the leading edge 305 of the label 220 into contact with the cartridge unit 70 while the cartridge unit 70 moves on the drum 100 between the location 225 (i.e., where the label is tagged to the cartridge unit 70) and the location 230 (i.e., where the tagged cartridge unit 70 is transferred to the rolling drum 235). In embodiments, the pressing roller 246 comprises a roller body having an outer surface 720 with flutes 725 formed therein. The flutes 725 are concave and have a shape that corresponds to the outer diameter of the housing of the cartridge unit 70. In implementations, the pressing roller 246 rotates in a direction opposite the direction of rotation of the drum 100. The rotational speed of the pressing roller 246 and the distance between flutes 725 on the pressing roller are configured relative to the rotational speed of the drum 100 and the distance between seats 115 on the drum 100 the such that a flute 725 comes into contact with a label 220 on a cartridge unit 70 as rotation of the drum 100 moves the tagged cartridge unit 70 past the pressing roller 246. In this manner, the flute 725 of the pressing roller 246 comes into contact with the leading edge 305 of the label 220 and presses the leading edge 305 against the outer surface of the cartridge unit 70, causing the adhesive on the underside of the label 220 to adhere the leading edge 305 to the outer surface of the cartridge unit 70.

In example embodiments, the pressing roller 246 is constrained to rotate in a single direction, e.g., by running against a stop pin in a drive hub face. In the example shown in FIG. 8, the pressing roller 246 is attached to a rotational shaft 800 having a gear 805 fixedly attached thereon. The gear 805 engages a gear 810 that is fixedly attached to a drive shaft that rotates the drum 100. In this manner, the pressing roller 246 is driven by the drum 100 and rotates in a direction opposite that of the drum 100. In embodiments, the gears 805 and 810 are configured with a gear ratio to rotate the pressing roller 246 at a speed relative to the drum 100 such that a respective flute 725 of the pressing roller 246 comes into contact with each tagged cartridge unit 70 carried on the drum 100. For example, a gear ratio of 3:1 may be used, such that the pressing roller 246 rotates three times as fast as the drum 100. Other gear ratios may be used. Alternatively, the pressing roller 246 may be driven independently of the drum 100, e.g., by a dedicated motor, an E-shaft, etc.

In accordance with aspects herein, the pressing roller 246 may be spring loaded relative to the shaft 800. In this manner, although the shaft 800 is driven only in a single direction, the pressing roller 246 may rotate a small angle relative to the shaft 800 in a direction opposite the rotation of the shaft 800. The spring loading of the pressing roller 246 on the shaft 800 provides additional pressure on the leading edge 305 of the label 220 against the cartridge unit 70 when a flute 725 of the pressing roller 246 comes into contact with the label 220 on the cartridge unit 70. The additional pressure provided by the spring loading helps ensure that the leading edge 305 is properly adhered to the cartridge unit 70. The spring loading may be provided by any suitable mechanism, such as a torsion spring connected between the pressing roller and the shaft 800.

In accordance with aspects herein, the pressing roller 246 may be spatially arranged relative to the drum 100 such that the pressing roller 246 depresses a seat 115 holding the cartridge unit 70 radially inward relative to the drum 100, e.g., in a manner similar to the described with respect to FIGS. 6a-6e. Specifically, the root diameter of the flute 725 combined with the location of the pressing roller 246 relative to the drum 100 can be configured to cause the flute 725 to remain in contact with the label 220 and cartridge unit 70 through an included angle of rotation of the drum 100. Maintaining the flute 725 in contact with the label 220 through the included angle of rotation in this manner increases the likelihood that the leading edge 305 of label 220 is successfully adhered to the cartridge unit 70 before the rolling process begins at the rolling drum 235. The included angle may be about 4 degrees, although other angles may be used.

The pressing roller 246 may be constructed with any suitable materials. For example, the pressing roller 246 may be composed of a polymer such as polyoxymethylene. In another example, the pressing roller 246 comprises a metal body that is coated, at least at the flutes 725, with a polymer. Implementations are not limited to these materials and any suitable materials may be used.

As described herein, the pressing roller 246 facilitates high speed labeling on single and dual track drum based labelers. For example, the system described herein enables driving the drum 100 at speeds greater than 1000 RPM while ensuring that the labels 220 are properly tagged to and wrapped around the cartridge units 70.

While the labeler system 200 has been described with respect to labeling cartridge units 70, it is understood that the labeler system 200 may also be used to apply labels to battery sections 72.

The particulars shown herein are by way of example and for purposes of illustrative discussion only and are presented in the cause of providing what is believed to be the most useful and readily understood description of the principles and conceptual aspects. In this regard, no attempt is made to show structural details in more detail than is necessary for fundamental understanding, the description taken with the drawings making apparent to those skilled in the art how the several forms disclosed herein may be embodied in practice.

It is noted that the foregoing examples have been provided merely for the purpose of explanation and are in no way to be construed as limiting. While aspects have been described with reference to an example embodiment, it is understood that the words which have been used herein are words of description and illustration, rather than words of limitation. Changes may be made, within the purview of the appended claims, as presently stated and as amended, without departing from the scope and spirit of the present disclosure in its aspects. Although aspects have been described herein with reference to particular means, materials, and/or embodiments, the present disclosure is not intended to be limited to the particulars disclosed herein; rather, it extends to all functionally equivalent structures, methods and uses, such as are within the scope of the appended claims.

The invention claimed is:

1. A system for applying a label to a vapor-generating article, comprising:
   a rotatable drum configured to hold a vapor-generating article;
   a tagging drum configured to tag a label to a housing of the vapor-generating article;
   a pressing roller arranged downstream from the tagging drum, the pressing roller configured to press a leading edge of the label against the housing while the vapor-generating article is in a seat of the rotatable drum; and
   a rolling drum arranged downstream from the pressing roller, the rolling drum configured to roll the label around the housing.

2. The system of claim 1, wherein the rotatable drum includes a drum body, a plurality of grooves in an outer face of the drum body, and a seat in each of the plurality of grooves, the seat including a seat groove that is configured to receive and hold the housing.

3. The system of claim 2, wherein the vapor-generating article is an electronic vapor device, the seat is composed of a plastic, and the housing is composed of a metal or metal alloy.

4. The system of claim 2, wherein the seat is moveable relative to the drum body along a radial direction of the drum body, the rotatable drum further including a resilient element configured to bias the seat outward along the radial direction.

5. The system of claim 4, wherein the pressing roller is configured to push the seat along the radial direction of the drum body when the leading edge of the label is pressed against the housing.

6. The system of claim 5, wherein the tagging drum is configured to push the seat along the radial direction of the drum body when the label is tagged to the housing.

7. The system of claim 6, wherein the tagging drum is configured to engage the housing through an included angle of rotation of the rotatable drum.

8. The system of claim 1, wherein the tagging drum is configured to adhere the label to the housing at an intermediate location of the label that is between the leading edge of the label and a trailing edge of the label.

9. The system of claim 8, wherein the intermediate location is closer to the leading edge of the label than the trailing edge of the label.

10. The system of claim 8, wherein the intermediate location is 1-2 mm from the leading edge of the label.

11. The system of claim 8, wherein the tagging drum is configured to adhere the label such that the leading edge of the label does not contact the housing.

12. The system of claim 1, wherein the pressing roller includes a roller body and a plurality of flutes in an outer face of the roller body.

13. The system of claim 12, wherein the pressing roller is configured to be driven relative to the rotatable drum such that one of the plurality of flutes contacts the leading edge of the label that is tagged to the housing and presses the leading edge of the label against the housing.

14. The system of claim 12, wherein the pressing roller is configured to rotate in a first direction, and the rotatable drum is configured to rotate in a second direction that is opposite to the first direction.

15. The system of claim 12, wherein the pressing roller is configured to rotate at a first speed, and the rotatable drum is configured to rotate at a second speed that is different than the first speed.

16. The system of claim 12, wherein the pressing roller is rotationally spring loaded.

17. The system of claim 1, wherein the pressing roller is smaller than the rotatable drum.

18. The system of claim 1, wherein the pressing roller includes alternately arranged fluted surfaces and planar surfaces.

19. A method of applying a label to a vapor-generating article, comprising:
   arranging the vapor-generating article in a seat on an outer surface of a rotatable drum configured to hold the vapor-generating article;

tagging a label to a housing of the vapor-generating article with a tagging drum;

pressing a leading edge of the label against the housing after the tagging with a pressing roller while the vapor-generating article is in the seat of the rotating drum, the pressing roller arranged downstream from the tagging drum; and rolling the label around the housing with a rolling drum after the pressing, the rolling drum arranged downstream from the pressing roller.

20. The method of claim 19, wherein the vapor-generating article is an electronic vapor device, the tagging is performed such that the leading edge of the label does not contact the housing, the pressing roller includes a roller body and a plurality of flutes in an outer face of the roller body, and the pressing roller is driven relative to the rotating drum such that one of the plurality of flutes contacts the leading edge of the label that is tagged to the housing and presses the leading edge of the label against the housing.

* * * * *